US00PP19565P2

(12) United States Plant Patent
Falstad

(10) Patent No.: US PP19,565 P2
(45) Date of Patent: Dec. 9, 2008

(54) ***HOSTA* PLANT NAMED 'SINGING IN THE RAIN'**

(50) Latin Name: ***Hosta* hybrid**
Varietal Denomination: Singing in the Rain

(75) Inventor: Clarence H. Falstad, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 11/881,885

(22) Filed: Jul. 30, 2007

(51) Int. Cl.
*A01H 5/00* (2006.01)

(52) U.S. Cl. ..... Plt./353

(58) Field of Classification Search ..... Plt./353
See application file for complete search history.

(56) References Cited

PUBLICATIONS

Walters Gardens, Inc. Plant Database, [online] [retrieved on May 31, 2008]. Retrieved from the Internet at <www-.waltersgardens.com/index.cfm?fuseaction=plants> 2 pp.*

* cited by examiner

*Primary Examiner*—Annette H Para
*Assistant Examiner*—June Hwu

(57) ABSTRACT

A new and distinct cultivar of *Hosta* plant named 'Singing in the Rain', characterized by leaves having creamy yellow to creamy white margins and a deep green center, with lavender flowers held nicely above foliage.

2 Drawing Sheets

Botanical classification: *Hosta* hybrid (Tratt.).
Variety denomination: 'Singing in the Rain'.

BACKGROUND OF THE INVENTION

The present invention relates to the new and distinct cultivar of *Hosta,* botanically known as *Hosta* hybrid (Tratt.), and hereinafter referred to as the cultivar 'Singing in the Rain'.

The new plant was discovered in 2002 by the inventor, Clarence H. Falstad, III, as a non-induced, naturally occurring whole-plant sport mutation of *Hosta* 'Blue Umbrellas' (not patented) in the plant tissue culture laboratory at a nursery in Zeeland, Mich. USA. Asexual propagation of the plant at the same nursery by tissue culture and division has shown that the unique and distinct characteristics of this new plant are stable and reproduce true to type in successive generations.

SUMMARY OF THE INVENTION

*Hosta* 'Singing in the Rain' is unique from its parent sport, *Hosta* 'Blue Umbrellas', and all other *hosta* cultivars, in several traits. *Hosta* 'Blue Umbrellas' is a very large *hosta* cultivar of unknown parentage having large dark green leaves with a slight glaucous surface. 'Singing in the Rain' has a blue-green to dark green center and a yellow to creamy white margin. This transition is only a seasonal phenotype change, and does not reflect any change in genotype. The following spring the plant emerges with the same yellow margins to the leaves.

The nearest comparison varieties are 'Dancing in the Rain' (U.S. Plant Pat. No. 15,977) *Hosta*'Blazing Saddles' (not patented) and *Hosta* 'Karin' (U.S. Plant Pat. No. 12,663). *Hosta* 'Karin' has more pointed leaves, and the margins lighten to a whiter color and are not as wide as 'Singing in the Rain'. *Hosta* 'Dancing in the Rain' has a lighter center and darker margin. *Hosta* 'Blazing Saddles' has as one of its parents 'Blue Umbrellas' but is more rugose with a lighter green leaf center than 'Singing in the Rain' and has a whiter leaf margin.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
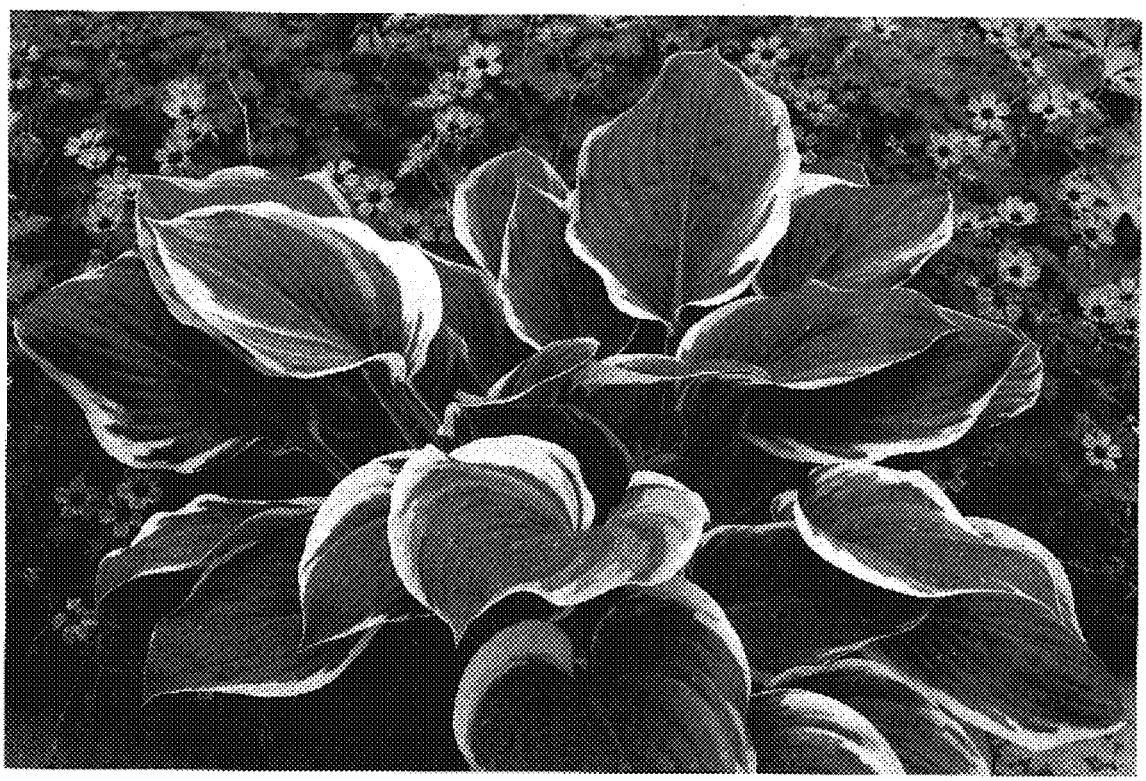
FIG. 1 shows of the plant with various margin colors.
Figure 2:
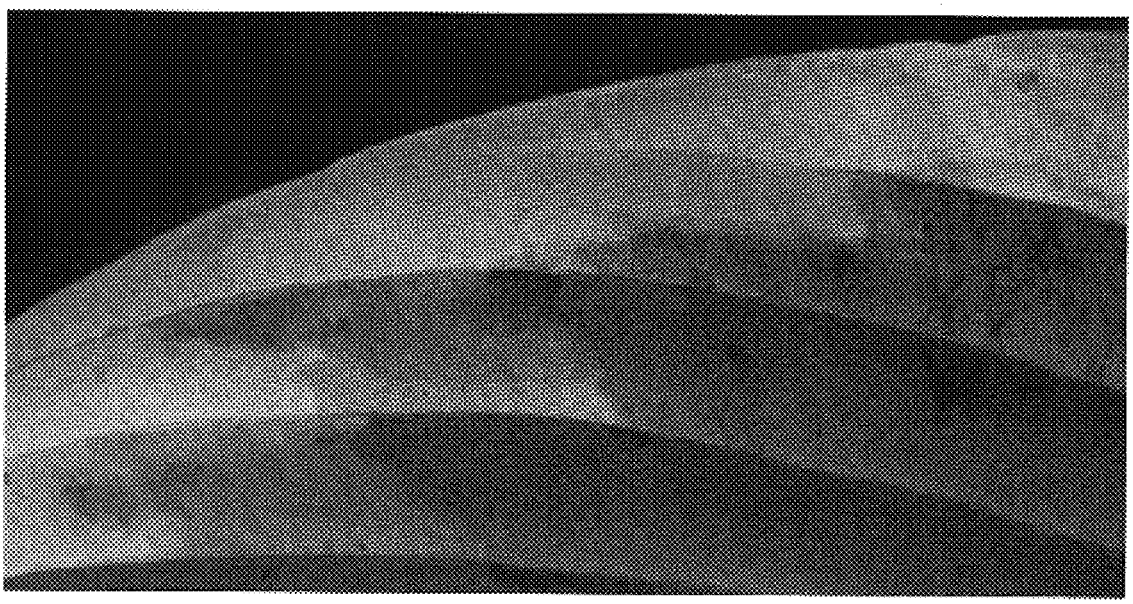
FIG. 2 shows a close-up of underside of the leaf.
Figure 3:
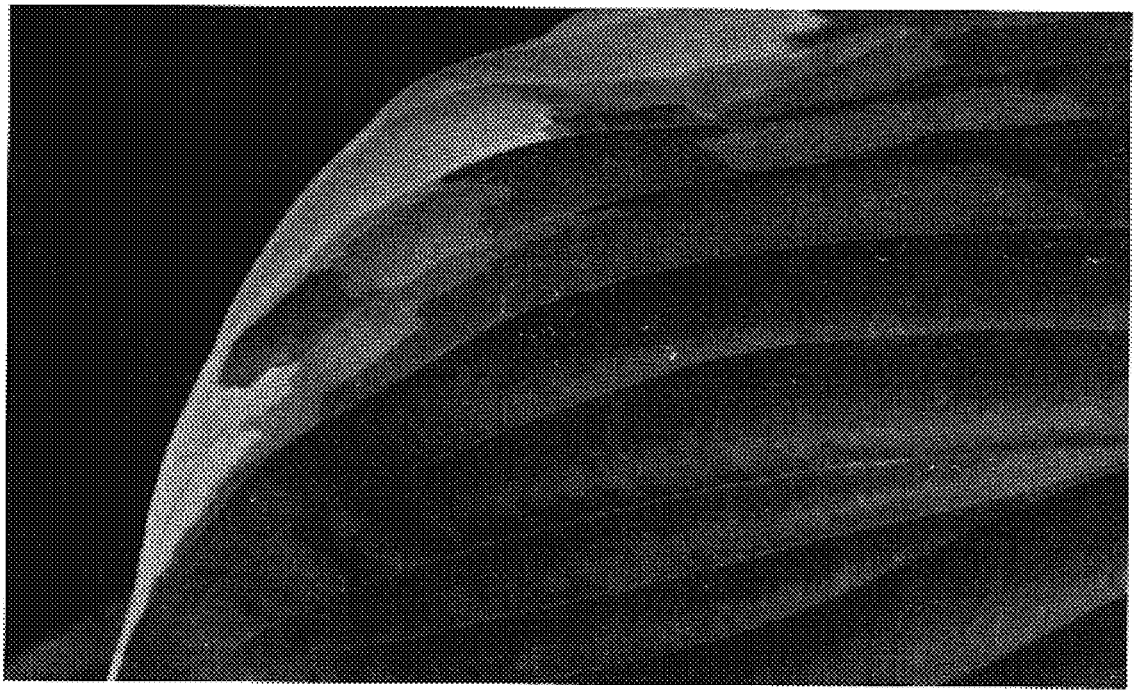
FIG. 3 shows a close up of the upper side of the leaf.

The following descriptions and color references are based on The Royal Horticultural Society Colour Chart (2001 edition) except where common dictionary terms are used. The new plant, *Hosta* 'Singing in the Rain', has not been observed under all possible environments. The phenotype may vary slightly with different environmental conditions, such as temperature, light, fertility and moisture, but without any change in the genotype. The following observations and size descriptions are of a three-year old plant in a shade trail garden in Zeeland, Mich., USA with supplemental water and fertilizer, under 50% shade on cloudless days, day temperatures of 15° to 34° degrees C., and night temperatures of 8° to 20° C.

Botanical classification: *Hosta* hybrid cultivar 'Singing in the Rain'.

Parentage: Naturally-occurring uninduced sport of *Hosta* 'Blue Umbrellas' (not patented).

Propagation: Method by tissue culture and division. Time to initiate roots from both division and tissue culture three to four weeks from cutting.

Rooting habit: Normal, fleshy, to 3 mm thick, lightly branched.

Plant habit: Herbaccous, densely rhizomatous perennial, symmetrical with radical leaves upright to slightly arching through flowering period, more horizontal late in the season and in maturity.

*Crop time.*—Under normal summer greenhouse growing conditions about 18 weeks to finish in a one-liter container; plant vigor is very good.

*Plant size.*—At flowering is 45 to 60 cm tall and 120 to 130 cm wide.

Foliage description:

*Shape and size.*—Ovate to broadly ovate leaf blades, with sharply acute apex when mature and cordate base, slight glaucous above becoming shiny, heavily glaucous below through season;

*Leaf blades.*—24 to 28 cm long and 16 to 22 cm wide.

*Color.*—Adaxial (upper) surface is a deep green closest to RHS 136A with a slight glaucous bloom in the center, the margin is between RHS 10A and RHS 11D; intermediate sections between the margin and center include RHS 188C with darker green undertone, RHS N138C, and RHS N144A; Abaxial margin surface is RHS 11D and the center is closest to RHS 122B and RHS 138A where the glaucous bloom is rubbed away, intermediate sections between the margin and center of RHS 122C, RHS N138D and lighter than RHS 139D;

*Leaf blade margins.*—Entire, the creamy yellow variegation pattern on the edge varies in different regions of the leaf and with different leaf maturities from 10 to 25 mm wide, in young immature plants margins are thinner, increasing as plants mature up to about seven to nine years-old.

*Petioles.*—30 to 38 cm long and 9 to 11 mm wide; center color RHS 138A, margin 10B to RHS 155D on both surfaces with a slight glaucous surface.

*Veins.*—Parallel, deeply impressed on top surface and protruding on bottom, same color as surrounding leaf tissue;

Flower description:

*Buds.*—Two days prior to opening the buds are violet RHS 85 D and RHS 85 A, 6 to 7 cm long, up to 1.5 cm wide,

*Flowers.*—21 to 45 per scape, funnel form, 4 to 6 cm wide and 6 to 8 cm long, (distal flowers being smaller); no detectable fragrance; persists for a normal period, up to two days, and the scapes remain effective from early July to late July.

*Tepals.*—Arranged in two layers of three, fused at base; with slightly-recurved acute apex; approximately 7 cm long and 1.2 cm wide, the inner three with clear 1 to 2 mm margin, base color in center of tepals Red purple RHS 69D and violet stripes of RHS 84 B. The base of the tepals is between RHS 75 B and 76 B.

*Bract.*—Subtending each one to two flowers; lowest bract 6 cm long and 2 cm wide, decreasing to 10 mm long and 6 mm wide; colors closest to RHS 137A in the center top surface, margin surface contains portions ranging from RHS 10A to RHS 155D; the underside margin between RHS 10B and RHS 10D, and the center RHS 138A;

*Peduncle.*—Angled and slightly arching, up to 48 cm long and 0.8 cm in diameter, glaucous texture producing and color RHS N138C, if glaucous wax is removed RHS 144A;

*Pedicel.*—Approximately 2 to 3 cm long, 3 mm wide, matte to slightly shiny surface. RHS 138D with slight lavender tinting if exposed to high sunlight;

*Gynoecium.*—Style — 5 to 6 cm long, 1 mm diameter, near white, lighter than RHS 155D, curled upward at distal end; Stigma — white, lighter than 155D, 2 to 3 mm diameter. Androecium — Filaments — six, white lighter than 155D, approximately 1 mm in diameter and to 5 cm long;

*Anthers.*—5 to 6 mm long, 1.5 mm wide, about RHS 83 A around margin of abaxial side, white in center, pollen is yellow-orange RHS 17 B.

*Fruit.*—Tri-valved dehiscent capsule, about 4.5 cm long and 0.8 cm wide, RHS 139A before drying; seeds — one-winged, about 1 cm long and 4 mm wide, RHS 200A; 45 to 60 per capsule;

Disease resistance: In side by side testing *Hosta*'Singing in the Rain' is more resistant to slugs than many other cultivars. It grows best with plenty of moisture but is able to tolerate some drought. Hardiness to at least USDA zone 3, and other disease resistance is typical of other *hostas*.

I claim:

1. A new and distinct cultivar of ornamental *Hosta* plant named 'Singing in the Rain' having deep green centered leaves, light yellow to cream white margins and light lavender flowers as herein described and illustrated, suitable as a potted plant, for landscaping specimen or in mass, and for florist type arrangements.

* * * * *